United States Patent [19]

Pratellesi et al.

[11] Patent Number: 5,244,637

[45] Date of Patent: Sep. 14, 1993

[54] TEST TUBE FOR BIOLOGICAL ANALYSES, PROVIDED WITH A DEVICE FOR CHECKING EFFICIENCY AND POSITION, FOR PHOTOMETRIC READINGS

[75] Inventors: Tiziano Pratellesi, Pontassieve; Antonio Ricci, Monteriggioni, both of Italy

[73] Assignee: Diesse Diagnostica Senese S.r.l., Milan, Italy

[21] Appl. No.: 818,102

[22] Filed: Jan. 8, 1992

[30] Foreign Application Priority Data

Jan. 10, 1991 [IT] Italy ............... FI/91/A 5

[51] Int. Cl.[5] .................................................. B01L 3/14
[52] U.S. Cl. .................................. 422/102; 422/99; 435/808; 435/296; 356/246
[58] Field of Search ............... 422/102, 99; 435/296, 435/808; 356/244, 246, 40; 220/662

[56] References Cited

U.S. PATENT DOCUMENTS

| | | | |
|---|---|---|---|
| 3,847,482 | 11/1974 | Sokol et al. | 356/40 |
| 4,254,223 | 3/1981 | Schuurs et al. | 435/296 |
| 4,257,709 | 3/1981 | Mostyn, Jr. | 356/40 |
| 4,265,538 | 5/1981 | Wertheimer | 356/246 |
| 4,451,434 | 5/1984 | Hart | 356/246 |
| 4,609,991 | 9/1986 | Minton et al. | 356/246 |
| 4,628,036 | 12/1986 | Scheepens et al. | 422/102 |
| 4,690,900 | 9/1987 | Kimmo et al. | 356/246 |

FOREIGN PATENT DOCUMENTS 0155836 12/1981 Japan .

Primary Examiner—Robert J. Warden
Assistant Examiner—Hien Tran
Attorney, Agent, or Firm—McGlew and Tuttle

[57] ABSTRACT

Test tube for biological analyses, and in particular for blood tests such as erythrocyte sedimentation rate, provided with a device making it possible to perform a photometric inspection of the test tube with a relative movement between the optical system and the test tube (1), the latter being between the emitter (E) and the receiver (R) of said system; the test tube possesses—externally on the base—a device in the form of an optical prism (5) that induces a sudden change in the direction of the light beam emitted by the emitter so that it briefly is unable to reach the receiver.

11 Claims, 1 Drawing Sheet

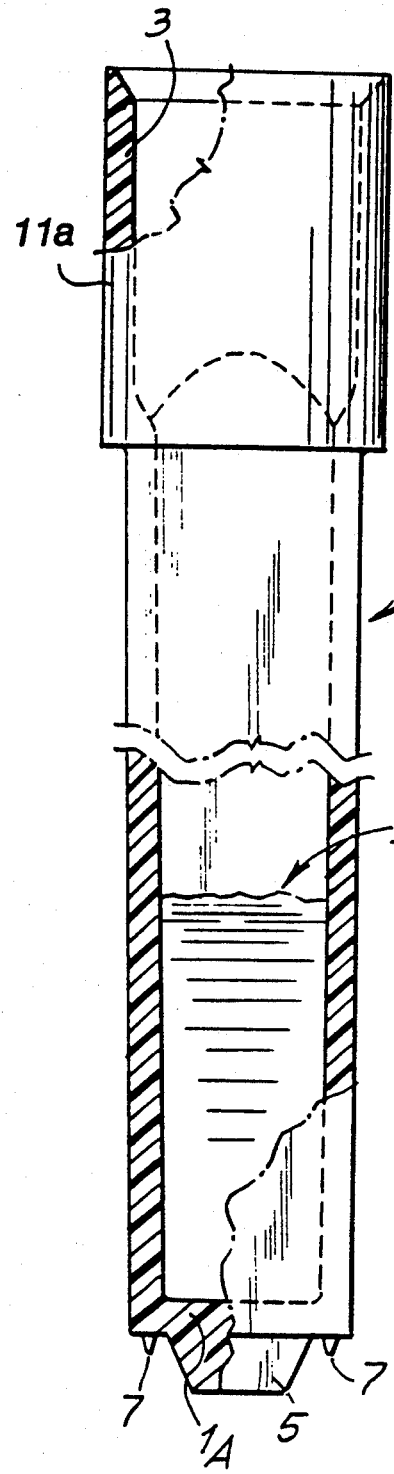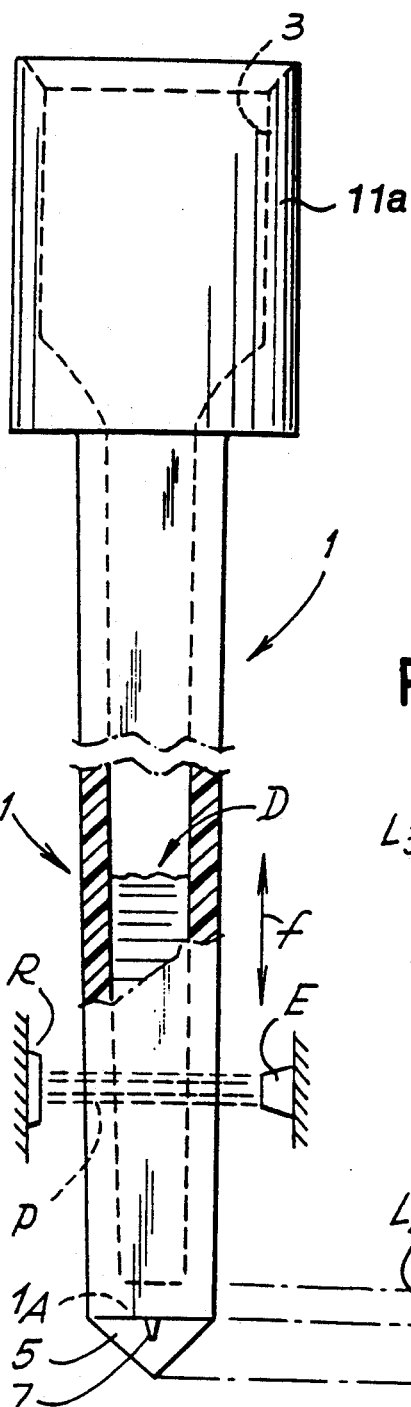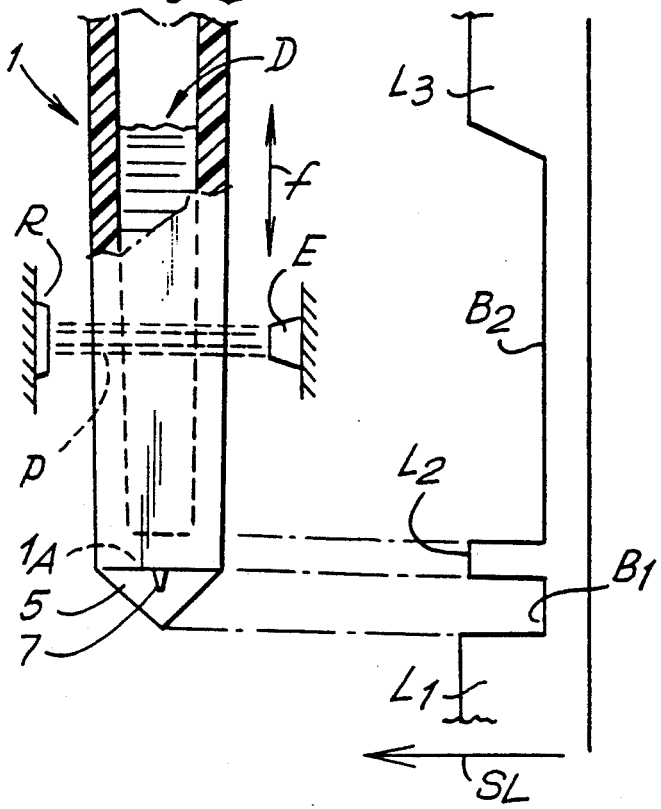

TEST TUBE FOR BIOLOGICAL ANALYSES, PROVIDED WITH A DEVICE FOR CHECKING EFFICIENCY AND POSITION, FOR PHOTOMETRIC READINGS

FIELD OF THE INVENTION

The invention relates to a test tube for biological analyses and in particular for blood tests, for example measuring the erythrocyte sedimentation rate (or E.S.R.) and other tests and analyses that can be performed with optical measuring instruments.

BACKGROUND OF THE INVENTION

With equipment of this kind, use is generally made of test tubes that may be of various shapes and sizes. To achieve a good level of automation and eliminate all sources of error, it is advisable to carry out a number of checks, especially checking that test tubes are present and that they have been correctly positioned in the instrument. In addition, it is always advisable to check the efficiency of the optical systems (emitter+receiver), so that errors of insertion and position of the test tubes are not inadvertently made.

SUMMARY AND OBJECTS OF THE INVENTION

In the present invention, the check for the presence of the test tube can in fact be made directly by the instrument's optical reading system and suitably controlled by a computer. The device of the invention also serves to check on the exact position of the test tube inside the instrument, since a test tube that is not fully inserted in its seat can—if the fault is not reported—give rise to bad data readings which may then cause sometimes very serious problems and errors. Another useful aspect of the invention is that it can automatically carry out a continuous and repeated check on the speed and inertia of response of the optical sensor, so as to avoid errors in the readings and in the results obtained from these.

These and other objects and advantages will become clear from the following more detailed description.

Basically, the test tube for biological analyses, makes it possible to perform an optical inspection through the test tube itself and with a relative movement between the optical system and the test tube. The latter being between the components (emitter and receiver) of the system. The invention possesses externally, on the base of the test tube, an optical prism that induces a sudden change in the direction of the light beam of said optical system, thereby giving rise to a "dark" signal in the receiver.

The optical prism can be an extension projecting from a flat thickness forming the transparent base of the test tube. The optical prism can be obtained directly from the molding of the transparent material that forms the test tube.

Advantageously the prism bounds a step formed along the outer edge of the base of the test tube.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:
FIGS. 1 and 2 show a test tube in two external views at right angles to each other, with parts being in section;
FIG. 3 shows a diagram of the strength of a light signal obtainable with the test tube of the invention.

DETAILED DESCRIPTION OF THE PREFERRED EMBODIMENT

As depicted in the accompanying drawing, 1 indicates a prismatically-shaped test tube of rectangular section with an upper end 11A forming the seat 3 for a stopper. The test tube has flat walls and in particular two walls of greater area and two walls of lesser area, so that the rectangular section has sides which are more or less greatly differentiated from each other. The optical analysis is performed by passing the test tube with a relative movement between an emitter E of a light ray and a receiver R of the light ray. The ray passing through the lesser thickness of the body of liquid that may be held in the test tube in the reading and analyzing instrument, and its path being that corresponding to the lesser dimension of the rectangular section. A relative movement, specifically an up-and-down movement indicated the double arrow f of FIG. 2, with respect to the optical system E and R, makes it possible to check for the presence of the test tube and of its contents. This is done in order for example to obtain a check of the transparency of the biological liquid held in the test tube and the position of the line of demarcation D between the nontransparent part (for example the corpuscular part of the blood) and the transparent part (for example plasma) of the biological liquid under test.

The improved test tube of the invention possesses in addition to the thickness of base wall 1A, externally to and beneath the test tube, an extension 5 in the form of an optical prism with its edge pointing down and parallel to the larger walls of the test tube. These walls pass the pencil of light energy P between the emitter E and the receiver R. The prism may be of any suitable shape and advantageously—though not necessarily—its active walls may be inclined by approximately 45° with respect to the test tube's plane of symmetry passing through the edge of the prism 5. Advantageously, the prism does not project directly from the intersection between the side walls and the base, but rather at a certain distance from the edges of these walls with the base, so as to create a step which gives a sharper differentiation in the optical behavior on passing between the prism portion and the base wall portion 1A. On this step there may also be the irregularities indicated generally by 7 arising from the point of injection of the thermoplastic material when the test tubes were formed by molding. These irregularities have no effect for the purposes of the indications supplied by the analyzing optical system.

The presence of a prism 5 at the base of the test tube offers many significant advantages.

The diagram of FIG. 3 shows the amount of light energy SL received by the receiver R and passing in the form of a pencil of light P, through the portion of the test tube inserted in a measuring instrument and the portion immediately below the bottom end of this test tube. Using the test tube of the invention the measuring instrument produces: a first zone of direct passage without attenuation of the energy of the pencil P and hence a phase L1 of unattenuated light. As soon as the pencil of light reaches the prism 5 in its relative movement with respect to the test tube, a sharply defined dark phase B1 is obtained, due to the change in the direction of the light beam caused by the prism; there follows a phase L2 caused by the passing of the light through the transparent thickness of the test tube base 1A. After the test tube base 1A, the pencil of light energy P will now pass through the more or less strongly opaque portion of the biological liquid under test, held in the test tube, where the opaque corpuscular part is concentrated. This produces a dark phase B2 corresponding to the denser and more opaque column of biological liquid, as far as the level D of separation between the opaque corpuscular part and the transparent part of said biological liquid. When the pencil of light reaches the level D, a light phase L3 is produced by the more or less sharp increase in transparency of the biological liquid above the level of demarcation D.

The light and dark signals L1, B1, L2 indicated above make it possible to perform many reliable checks; these are made possible by the presence of the prism 5, which by changing the direction of the pencil of light creates the sharp demarcation between the light zones L1 and L2 and the dark zone B1, this last being due to the change in the direction of the pencil of light caused by the prism 5. This sequence remains true and valid even if there is no biological liquid in the test tube.

The sequence of illuminations and interruptions in the illumination of the receiver R provides in the first place a check of the efficiency of the optical system of the instrument, thereby avoiding those perturbations in the accuracy of the readings which may be due even to an attenuation in the efficiency of the system itself. Another possibility offered by the arrangement described above is that of precisely reading the position of the test tube and hence checking that the test tube is correctly positioned which excludes a reading error due to bad position of the test tube, which is otherwise difficult to check for from other criteria. Still another possibility offered by the test tube of the invention is that of directly checking for the presence of the test tube using the same signals which among other things also identify its position. Again, the sharp separations between the dark zones and the light zones, which are offered by the directional change caused by the prism 5, enable the speed and inertia of response of the sensor to be checked, particularly by the presence of the flash of light L2 obtained through the more or less narrow thickness 1A of the definitely transparent base of the test tube.

It should be noticed that the step between the test tube base wall 1A and the prism extension 5 ensures the clear separation of the dark zone B1 from the light zone L2, which zones are quite unaffected by possible irregularities such as those due to the injection points which, as regards the irregularities 7, are provided in the mold for the injection molding of the test tubes using synthetic thermoplastics.

These and other advantages and possibilities of reliable checks, offered by the test tube of the invention, represent an improvement in the functionality of analytical equipment of the type indicated.

It will be understood that the drawing shows only an illustrative embodiment which is given purely as a practical demonstration of the invention, it being possible for said invention to vary as regards shapes and arrangements without thereby departing from the scope of the concept underlying said invention.

We claim:

1. A test tube apparatus for analyzing fluid, the test tube comprising:
    a cylinder having walls transparent to a beam of light passing through said cylinder in a substantially radial direction, said cylinder has a radial cross-sectional shape substantially similar to a parallelogram;
    optical prism means for receiving the radial beam of light on a first side and substantially barring the radial beam of light from exiting said optical prism means on a second side, said second side being substantially radially opposite said first side, said optical prism means being positioned on an axial end of said cylinder.

2. A test tube in accordance with claim 1, further comprising:
    a base portion positioned between said optical prism means and said axial end of said cylinder and said base portion sealing said axial end of said cylinder, and said base portion being transparent to the radial beam of light and said base portion being of a predetermined thickness.

3. A test tube in accordance with claim 2, wherein:
    said optical prism means projects from said base portion.

4. A test tube in accordance with claim 2, wherein:
    said optical prism means, said base portion and said cylinder being molded of a same transparent material.

5. A test tube in accordance with claim 2, wherein:
    said optical prism means projects from a step formed along an outer edge of said base portion.

6. A test tube in accordance with claim 1, wherein:
    said first and second sides of said optical prism means are angled with respect to the radial beam of light to deflect the radial beam of light by diffraction.

7. A test tube in accordance with claim 6, wherein:
    said optical prism means deflects said radial beam of light in an axial direction.

8. An optical analysis system for analyzing fluid, comprising:
    a cylinder having walls transparent to a beam of light passing through cylinder tube in a substantially radial direction;
    a base portion sealing an end of said cylinder, said base portion also being transparent to the radial beam of light passing through the cylinder, said base portion being of a predetermined thickness;
    optical prism means for receiving the radial beam of light on a first side and barring the radial beam of light from exiting said optical prism means on a second side in a radial direction, said second side being substantially radially opposite said first side, said optical prism means being positioned on side of said base portion opposite said cylinder;
    emitter means positioned adjacent to a first radial side of said cylinder and for emitting the radial beam of light in said substantially radial direction;
    receiver means positioned adjacent to a second radial side of said cylinder and substantially radially opposite to said emitter means, said receiver means receiving the radial beam of light in a substantially radial direction; and
    movement means for together moving said cylinder, said base portion and said optical prism means in between said emitter and receiver means in a substantially axial direction.

9. An optical analysis system in accordance with claim 8, wherein:
said cylinder is prismatic and has a radial cross-sectional shape substantially similar to a parallelogram.

10. The optical analysis system in accordance with claim 8, wherein:
said movement means is constructed and arranged to move said optical prism means between said emitter and receiver means produce a dark phase at said receiver means, and to move said portion base between said emitter and receiver means produces a light phases at said receiver means, said light and dark phase being used for calibration and checking.

11. A method for analyzing the fluid inside a test tube, the method comprising:
providing a test tube with a cylinder having walls transparent to a beam of light passing through the test tube in a radial direction, a base portion sealing an end of said cylinder, said base portion being of a predetermined thickness, an optical prism means for receiving the radial beam of light on a first side and barring the radial beam of light from exiting said optical prism means on a second side in said radial direction, said second side being substantially radially opposite said first side, said optical prism means being positioned on a side of said base portion opposite said cylinder; and emitting a beam of light in a direction substantially radial to said test tube;

relatively passing said test tube through the radial beam of light in a substantially axial direction;

receiving the emitted beam of light in a radial direction on a side of said test tube substantially opposite from said emitting of the radial beam of light; recording a dark phase when said optical prism means passes through the radial beam of light;

recording a light phase when said base portion passes through the radial beam of light; and determining presence, position and speed of said test tube, as well as efficiency and responsiveness of said emitting and receiving, from said dark phase and said light phase.

* * * * *